United States Patent [19]

Baucom

[11] Patent Number: 4,546,184
[45] Date of Patent: Oct. 8, 1985

[54] PERFLUORO-KETO-YLIDS AS PRECURSORS OF POLYCHLOROKETONES, 1,2-DIKETONES AND QUINOXALINES

[75] Inventor: Keith B. Baucom, Gainesville, Fla.

[73] Assignee: SCM Corporation, New York, N.Y.

[21] Appl. No.: 497,006

[22] Filed: May 23, 1983

[51] Int. Cl.$^4$ .................. C07D 241/42; C07D 403/04; C07B 9/00; C07B 7/00
[52] U.S. Cl. ..................................... 544/353; 568/312; 568/316; 568/323; 568/325
[58] Field of Search ................ 544/353; 568/316, 312, 568/325, 323

[56] References Cited

U.S. PATENT DOCUMENTS

| | | | |
|---|---|---|---|
| 3,642,700 | 2/1972 | Augl | 528/226 |
| 3,661,850 | 5/1972 | Stille | 528/126 |
| 3,766,141 | 10/1973 | Augl | 528/128 |
| 4,024,163 | 5/1977 | Elliott et al. | 560/8 |
| 4,046,814 | 9/1977 | Harris et al. | 568/314 |
| 4,082,806 | 4/1978 | Harris et al. | 568/316 |

OTHER PUBLICATIONS

House, "Modern Synthetic Reactions, 2nd Ed", p. 692.

*Primary Examiner*—Mark L. Berch
*Attorney, Agent, or Firm*—R. A. Sturges; T. M. Schmitz

[57] ABSTRACT

The invention relates to a novel fluorinated pre-polymer and novel process steps in producing the same. The pre-polymers are quinoxaline materials derived by reaction of diketone linkage containing perfluoro-compounds with an aromatic diamine. The diketone is produced by oxidatively dechlorinating a polychloroketone which may be a monoketone or a bis-ketone. The polychloroketone is produced by reacting a keto-ylid with a chlorinating agent, e.g., chlorine. The keto-ylid is produced by reacting a phosphorane with an acid halide of a polyoxy-perfluoroalkylene oxide wherein the perfluoro-oxyalkylene group contains two or three carbon atoms, and there are present from two to twenty perfluoro-oxyalkylene units in the oligomer. The quinoxalines, the polychloroketones and the diketones hereof are novel products. Cross-linking may be effected with a free radical generator.

28 Claims, 8 Drawing Figures

PERFLUORO-KETO-YLIDS AS PRECURSORS OF POLYCHLOROKETONES, 1,2-DIKETONES AND QUINOXALINES

The U.S. Government has a paid-up license in this invention and the right in limited circumstances to require the patent owner to license others on reasonable terms as provided for by the terms of Contract No. F33615-80-C-5129 awarded by Elastomers and Coatings Branch Nonmetallic Materials Division, Air'Force Materials Laboratory, Wright-Patterson AFB.

This invention relates to perfluoro compounds in which a substantial portion of the molecule consists of carbon atoms wherein the normally present hydrogen atoms have been replaced with fluorine atoms. More particularly, this invention relates to novel perfluoro polyether quinoxaline pre-polymers and novel intermediates and processes for producing the same. The prepolymers are particularly useful in the production of elastomeric polymers by cross-linking the quinoxalines with a free radical generator, e.g., an organic peroxide. The resulting elastomers are useful in forming seals and gaskets.

BACKGROUND OF THE INVENTION AND PRIOR ART

A principal object of the present invention is to provide practical synthesis for fluorocarbon ether elastomers for use in wide temperature band environments.

The thermal stability and low temperature flexibility of fluorocarbon ether linkages were recognized in the early 1950's. Various studies have shown that the fluorocarbon ether system is flexible at temperatures below 0° C., resistant to organic fluids, and thermally stable in the +300° C. to 400° C. range. The major problems have been, however, low molecular weight and lack of a curing system which gives a cross-linking bridge with stability equal to that of the polyeiher backbone.

Elastomeric polymers have been prepared from difunctional prefluoropolyether prepolymers by cross-linking through condensation or addition reactions. However, all of these systems have had at least one deficiency which has made them unsatisfactory for purposes requiring a wide temperature band and stability under hydrolytic and oxidative conditions.

Polyether elastomer systems which have perfluoropolyether segments or blocks in the backbone utilize perfluoro polyethers derived from perfluorinated epoxides, e.g., hexafluoropropylene oxide and tetrafluoroethylene oxide. Except for polycarbonyl fluoride systems, no other method for producing functionalized perfluoropolyethers is known. All polymerizations of perfluorinated epoxides are of an anionic nature. More specifically, they are all fluoride catalyzed polymerizations even though some other nucleophile may have been used as the initiator. These polymerizations involve high rates of chain transfer (fluoride ion exchange) and consequently relatively low molecular weight materials are obtained.

This is especially evident in the hexafluoropropylene oxide (HFPO) system when the desired products are to be difunctional. After only a few epoxide units have been added to the perfluorodiacid fluoride, monofunctional homooligomers of the epoxide begin to arise. This is intolerable because difunctionality is the highest importance for prepolymers. Maximum difunctionality can be assured in the HFPO system if low molecular weight materials of no more than eight perfluoro-oxyalkylene units are added to the diacid fluoride. Difunctional oligomer materials can be isolated from the homooligomers by careful fractional distillation. Polymers deriving their perfluoropolyether segment from HFPO do not maintain flexibility well at subzero temperatures as low as about −50° C.

Tetrafluoroethylene oxide (TFEO), the only other practical epoxide useful in making perfluoropolyethers is not commercially available because of its instability. Although it can be stored for several months at −78° C., at higher temperatures or even at −78° C. under improper condtions, it will rearrange to trifluoroacetyl fluoride. Under proper condtions, TFEO can be made and polymerized to materials which are very useful for the purposes hereof. See for example U.S. Pat. No. 3,250,806. It has been found that TFEO is especially useful for oligomerization using perfluoro-oxaglutaryl fluoride (Example XLII below). With this acid fluoride, TFEO reacts to give polyfunctional oligomers of very narrow molecular weight distribution and without any monofunctional homooligomers. These results are not both achieved in the oligomerization of TFEO with other acid fluorides. Although in several instances the reaction does not yield homooligomers, it does give oligomers of a fairly wide molecular weight distribution.

Elastomeric polymers which derive their perfluoropolyether segment from TFEO remain flexible at temperatures lower than similar elastomers which derive their perfluoropolyether segment from HFPO, and hence, where lower temperatures are encountered at which flexibility is required, the TFEO derived elastomers are preferred.

Perfluoropolyethers prepared from hexafluoropropylene oxide and tetrafluoroethylene oxide are described in the U.S. Pat. Nos. to Warnell 3,250,806 and Gerhard et al 3,250,807 which are incorporated herein by reference.

It has further been found that quinoxalines provide a suitable backbone member in the polymer because of their stability to heat and oxidative conditions. The alpha-diketones and bis(alpha-diketones) reactive with o-arylene diamines to give the quinoxalines, are conveniently produced starting with the keto-ylids and subsequently chlorinating to yield the dichloroketones and bis(dichloroketones). The quinoxalines hereof are useful to produce by cross-linking, polyquinoxalines which remain flexible over the desired wide temperature band and have the desired stability characteristics.

BRIEF STATEMENT OF THE INVENTION

Briefly stated, therefore, the present invention is in a process for making a quinoxaline which comprises reacting a phosphorane with an acid halide of a polyoxy perfluoro-alkylene oxide derived from hexafluoro-propylene oxide or tetrafluoroethylene oxide and the number of perfluoro-oxyalkylene units is from 2 to 10 to form a keto-ylid. The keto-ylid, in a novel step, is then chlorinated using any suitable chlorinating agent, e.g., elemental chlorine, to form a polychloroketone. The polychloroketone is useful to form a diketone structure by a novel process of dechlorinating and oxidizing with a dechlorinating-oxidizing agent, such as silver trifluoroacetate. Also, the 1,2-diketone or bis-(1,2-diketone) may be directly oxidized with an organic peroxy acid, e.g., m-chloroperoxybenzoic acid peroxybenzoic acid, peracetic acid, etc. The diketones hereof, also novel compounds, are then reacted by a novel step with an ortho-arylene diamine, e.g., ortho-phenylene diamine to form the pre-polymer quinoxaline, the latter being a novel precursor cross-linkable to the desired polymers.

The novel polyketones of the present invention have the general formula:

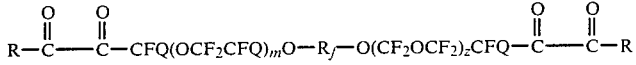

wherein R is phenyl or alkylphenyl, e.g., tolyl, xylyl, p-ethylphenyl, p-isopropylphenyl, p-t-butylphenyl, etc.; $R_f$ is $(CF_2)_y$ where y is an integer from 2–6 or $(CF_2OCF_2)_z$ where z is from 1 to 20; Q is F, or $CF_3$; and m and n are independently selected from 0 to 18. Preferably, m and n are equal and in the range of from 8 to 16.

BRIEF DESCRIPTION OF THE DRAWINGS

The invention illustrated with specific examples below which refer to the annexed drawings which are liquid film infrared scans of the products obtained in the respective examples. In the annexed drawings, therefore.

DETAILED DESCRIPTION AND SPECIFIC EXAMPLES

Figure 1:
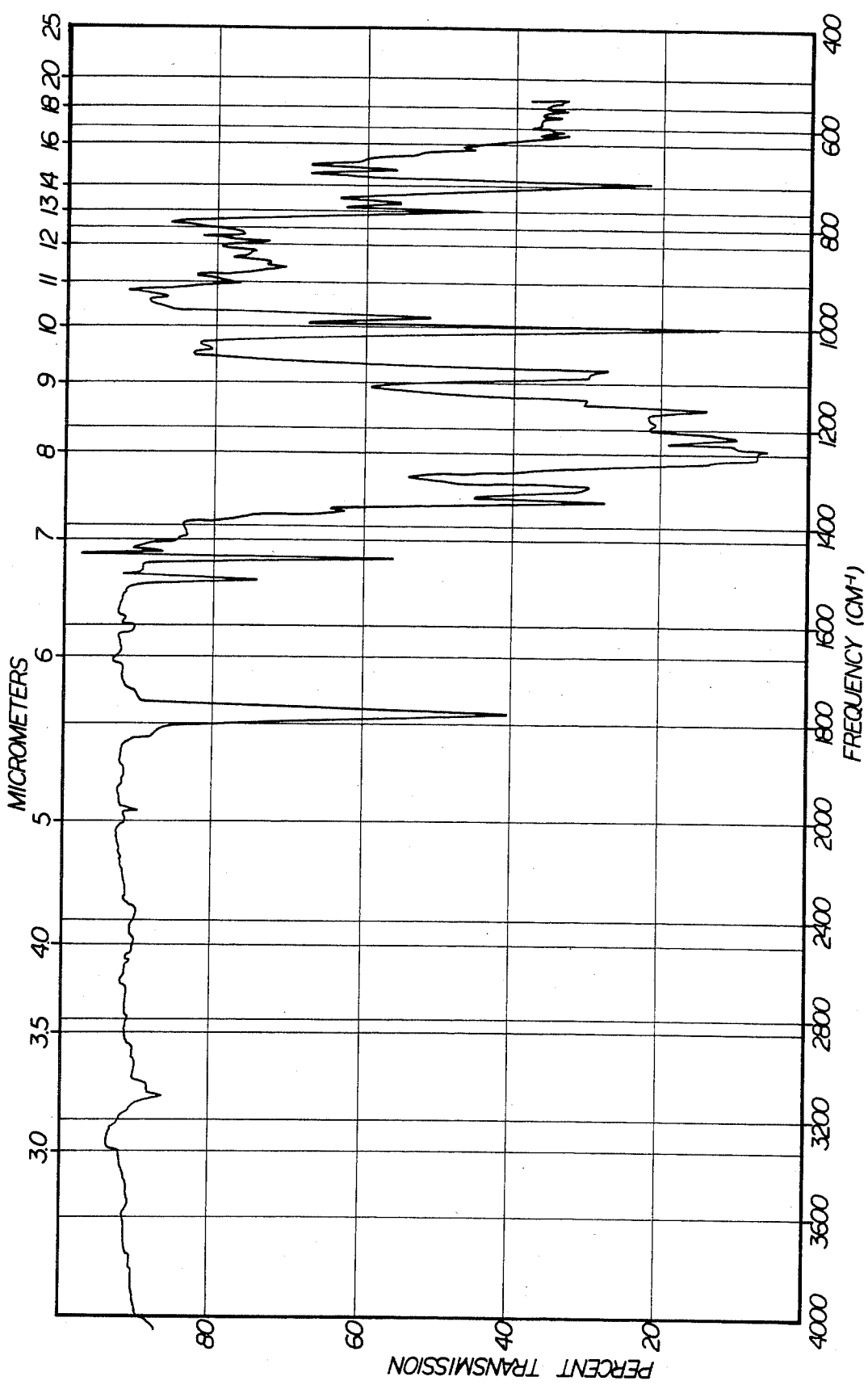
FIG. 1 is a liquid film on NaCl plates scan of the product of Example IIIa.

As indicated above, the starting materials for preparation of the quinoxaline pre-polymers are alkylene epoxides in which all of the hydrogen normally in the epoxide has been replaced by fluorine. Only two alkylene epoxides have been found useful herein; namely, tetrafluoroethylene oxide and hexafluoropropylene oxide structures represented by the following, respectively.

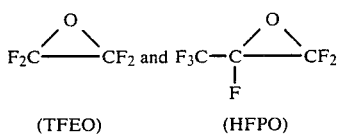

(TFEO)                (HFPO)

The polyoxy perfluoro-alkylene oxide and chloride is prepared from the acid fluoride by hydrolysis and treatment with $SOCl_2$. With HFPO, when forming a monofunctional material the polyoxy perfluoro-alkylene oxide and chloride has the following general formula:

wherein n is from 0 to 20. The unit $(-CF(CF_3)-CF_2-O-)$ is identified herein as a perfluoro-oxy-alkylene unit.

With TFEO, the general formula is:

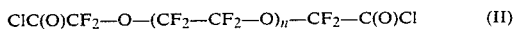                (II)

wherein n is from 0 to 20. The perfluoro-oxyalkylene unit is $(-CF_2-CF_2-O-)$.

Compounds (I) and (II) above which are acid halides (chlorides) are then reacted with a phosphorane to form a keto-ylid. The phosphorane, or ylid, is formed by reacting an arylphosphine, e.g., triphenyl phosphine with a $C_2-C_{10}$ alkyl or cycloalkyl halide, e.g., cyclohexyl iodide, bromide or chloride; benzychloride, iodide, or bromide; ethyl chloride, bromide, or iodide, butylchloride, bromide or iodide, decyl chloride, bromide, iodide, etc., according to the following scheme.

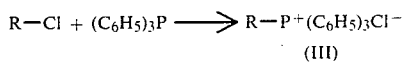
(III)

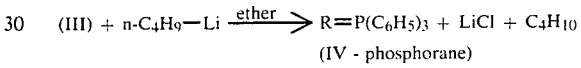
(IV - phosphorane)

The polyoxy-perfluoro alkylene oxide acid chloride (I) or (II) is then reacted with (IV) benzyl triphenyl phosphorane to yield a keto-ylid as follows:

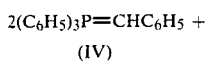
(IV)

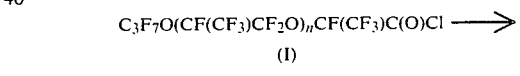
(I)

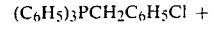

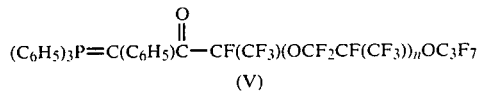
(V)

Compound (V) is the desired keto-ylid. If TFEO had been the source of the polyoxy-perfluoro alkylene oxide, the keto-ylid may be a bis-(keto-ylid), or a mono-(keto-ylid).

Compound (V) is then chlorinated, preferably with elemental chlorine to yield a dichloroketone, or a bis-dichloroketone depending on whether the starting epoxide is HFPO or TFEO, respectively, as follows:

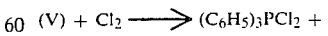

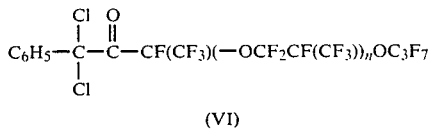
(VI)

or,

-continued $$(V) + Cl_2 \longrightarrow (C_6H_5)_3PCl_2 +$$

$$\underset{(VII)}{C_6H_5\overset{Cl}{\underset{Cl}{\overset{|}{C}}}-\overset{O}{\overset{\|}{C}}-(CF_2OCF_2)_n\overset{O}{\overset{\|}{C}}-\overset{Cl}{\underset{Cl}{\overset{|}{C}}}-C_6H_5}$$

The product (VI) or (VII) is then oxidatively dechlorinated according to the following schemes to yield a diketone (VIII) or bis-(diketone) (IX), respectively:

$$(VI) + 2CF_3COOAg + H_2O \longrightarrow$$

$$\underset{(VIII)}{C_6H_5\overset{O}{\overset{\|}{C}}-\overset{O}{\overset{\|}{C}}-CF(CF_3)(OCF_2CF(CF_3))_nOC_3F_7} +$$

$$2AgCl + 2CF_3COOH$$

$$(VII) + 2CF_3COOAg + H_2O \longrightarrow$$

$$\underset{(IX)}{C_6H_5\overset{O}{\overset{\|}{C}}-\overset{O}{\overset{\|}{C}}-(CF_2OCF_2)_n\overset{O}{\overset{\|}{C}}-\overset{O}{\overset{\|}{C}}C_6H_5}$$

The product (VIII) or (IX) is then reacted with an ortho-arylene diamine or a bis-(o-arylenediamine) to yield the desired quinoxaline.

$$(VIII) + o\text{-}C_6H_4(NH_2)_2 \longrightarrow$$

(X) $C_3F_7O(CF(CF_3)CF_2O)_nCF(CF_3)$ — quinoxaline structure with $C_6H_5$ group (IX) + tetramine $\longrightarrow$ polyquinoxaline.

It becomes convenient at this point to illustrate the foregoing schemes by giving illustrative examples, it being understood that such examples are for illustrative purposes and not to be construed as limiting the invention to the scope thereof.

EXAMPLE I

Preparation of (HFPO)₂ Acid Chloride

A five-liter, three-necked, round-bottom flask was equipped with a magnetic stirrer, dropping funnel, thermowell, and condenser backed by a Dry Ice-acetone trap. A mixture of (HFPO)$_n$ acids (n=2, 3, 4, etc.) were placed in the flask, 100 ml of pyridine were added, and the mixture heated to 70° C. while being stirred. Thionyl chloride (1200 ml) was added over a three-day period and, after the reaction had subsided, a partial vacuum (10 mm Hg) was applied. All products which distilled from the flask at 55° C. or less were collected and redistilled on an Oldershaw column to give 600 g of 92% acid chloride. This material was distilled on a 40-plate Oldershaw column to give 440 g of 99+% pure (HFPO)₂ acid chloride. The acid chloride had an i.r. scan as shown in FIG. 1. chloride This material was distilled on a 40-plate Oldershaw column to give 440 g of 99+% pure (HFPO)₂ acid chloride. The acid chloride had an i.r. scan as shown in FIG. 1.

EXAMPLE II

Preparation of (HFPO)₂ Keto-ylid

The preparation of (HFPO)₂ derived keto-ylid was carried out three times with an average yield of 71%.

EXAMPLE IIa

Preparation of (HFPO)₂ Keto-ylid

A five-liter, three-necked flask was equipped with a thermowell, magnetic stirrer, condenser, backed by a liquid oxygen trap, and an additional funnel. The flask was swept with dry nitrogen before 2.5 liters of dry diethyl ether and 390 g of benzyltriphenylphosphonium chloride were added. The butyllithium (1 mole) was then added dropwise via the dropping funnel with the resulting bright orange color showing immediate reaction. The (HFPO)₂ acid chloride (174 g) was then slowly added over a two-hour period and the mixture was stirred overnight. The material was filtered, and solvent removed to give a thick oil which solidified when hexane was added. The product (203 g, 65% yield) was filtered and dried.

EXAMPLE IIb

Preparation of (HFPO)₂ Keto-ylid

The preparation of (HFPO)₂ keto-ylid was repeated to give additional material. A five-liter, three-necked flask was equipped with a mechanical stirrer, a thermometer, an addition funnel, and a condenser before bing charged with benzyltriphenylphosphonium chloride (390 g) and 2.5 liters of dry diethyl ether. One mole of butyllithium was added dropwise over a one-hour period with the characteristic change to a bright orange color noted. After the mixture was stirred for an additional two hours, the (HFPO)₂ acid chloride (175 g) was added. The mixture was stirred overnight and filtered the following morning. The ether was removed on a rotavap to give a thick oil which gave a nice solid when triturated with hexane. Filtration and drying gave 237 g (71% yield) of the desired (HFPO)₂ keto-ylid.

EXAMPLE IIc

Preparation of (HFPO)₂ Keto-ylid

A three-liter, three-necked flask was equipped with a magnetic stirrer, thermowell, addition funnel, condenser, and placed in a cooling bath. Ethyl ether (1.5 liter) was added along with 195 g of benzyltriphenylphosphonium chloride. The butyllithium (0.5 mole) was added over a 30-minute period and the mixture turned bright orange. The mixture was stirred for one hour, and the (HFPO)₂ acid chloride (87 g, 0.25 mole) was added over a 30 minute period. The mixture was stirred for one hour, the (HFPO)₂ acid chloride (87 g, 0.25 mole) was added over a 30-minute period. The mixture was stirred overnight before being filtered and the solvent was removed to give a reddish brown solid product which was washed with n-hexane and dried under vacuum to give 126 g (76% yield) of pure keto-ylid.

c. Reactions with (HFPO)₂ Keto-ylid

1. Attempted oxidation of (HFPO)₂ Keto-ylid with 90% Hydrogen Peroxide

A 25-ml, one-necked flask was equipped with a magnetic stirrer, and septum. The (HFPO)$_2$ keto-ylid (1 gram) was added to 10 ml reagent acetone and stirred in an ice bath as the hydrogen peroxide (0.2 cc, 90%) was added via a syringe. Since no reaction was evident after 16 hours, (0.5 cc) additional H$_2$O$_2$ was added and the mixture warmed to room temperature. Another 0.5 cc of hydrogen peroxide was added after 16 additional hours and the mixture stirred for eight more hours. There was no reaction as evidenced by recovered (HFPO)$_2$ keto-ylid.

2. Attempted Oxidation of (HFPO)$_2$ Keto-ylid using Oxygen and Sulfuryl Chloride A 250-ml, three-necked flask was equipped with a magnetic stirrer, a thermometer, a gas inlet, a dropping funnel, and a condenser. The (HFPO)$_2$ keto-ylid (13.2 g) was dissolved in Freon 113 (100 ml) and stirred as oxygen was bubbled through the system. The sulfuryl chloride (2.7 g) was added dropwise over a 45-minute period. The only product isolated was the salt C$_3$F$_7$OCF(CF$_3$)C(O)C(C$_6$H$_5$)ClP+(C$_6$H$_5$)$_3$Cl—.

3. Chlorination in a Stainless Steel Autoclave

Figure 4:
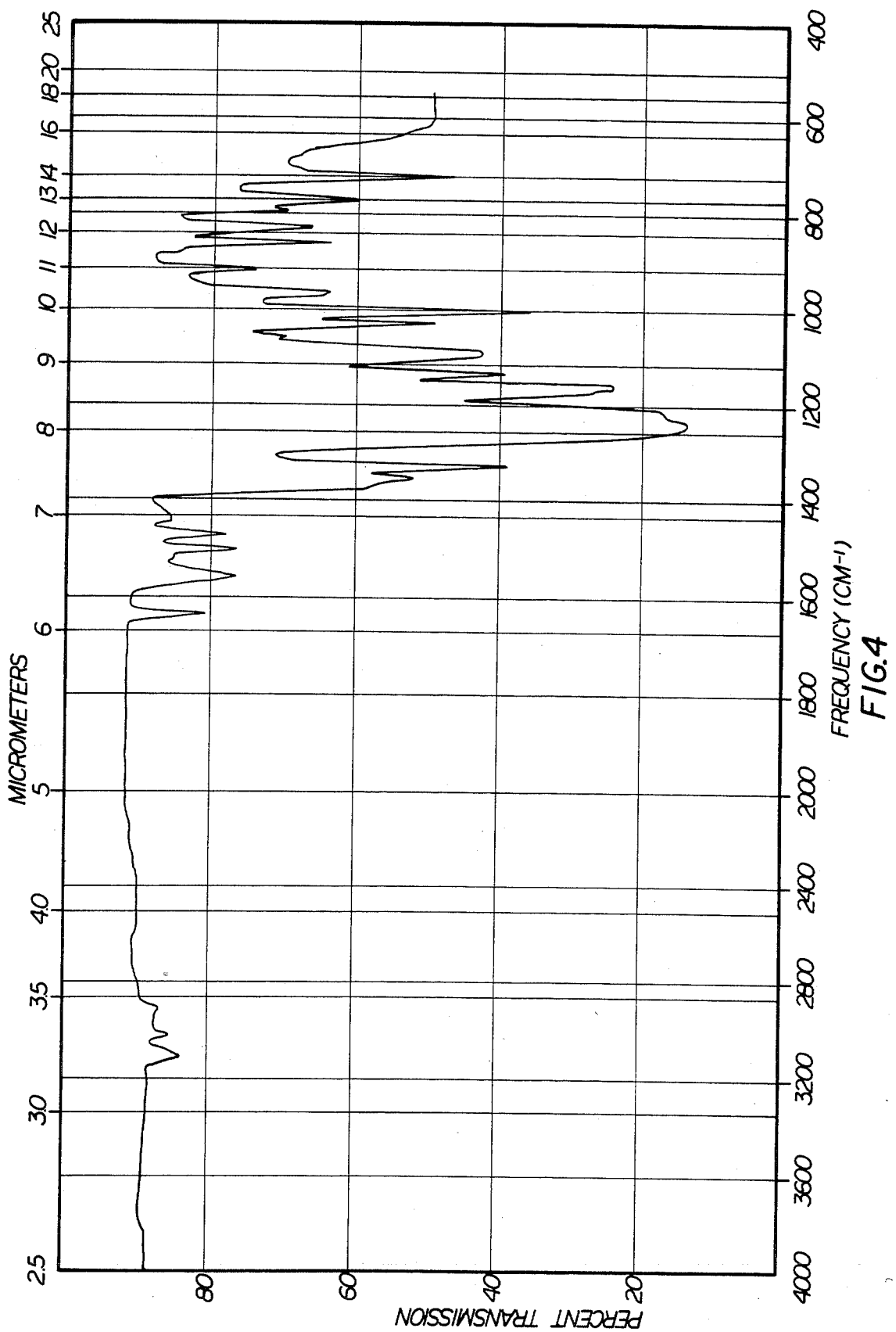
FIG. 4 is a liquid film scan of the bis-quinoxaline of Example Va.
Figure 5:
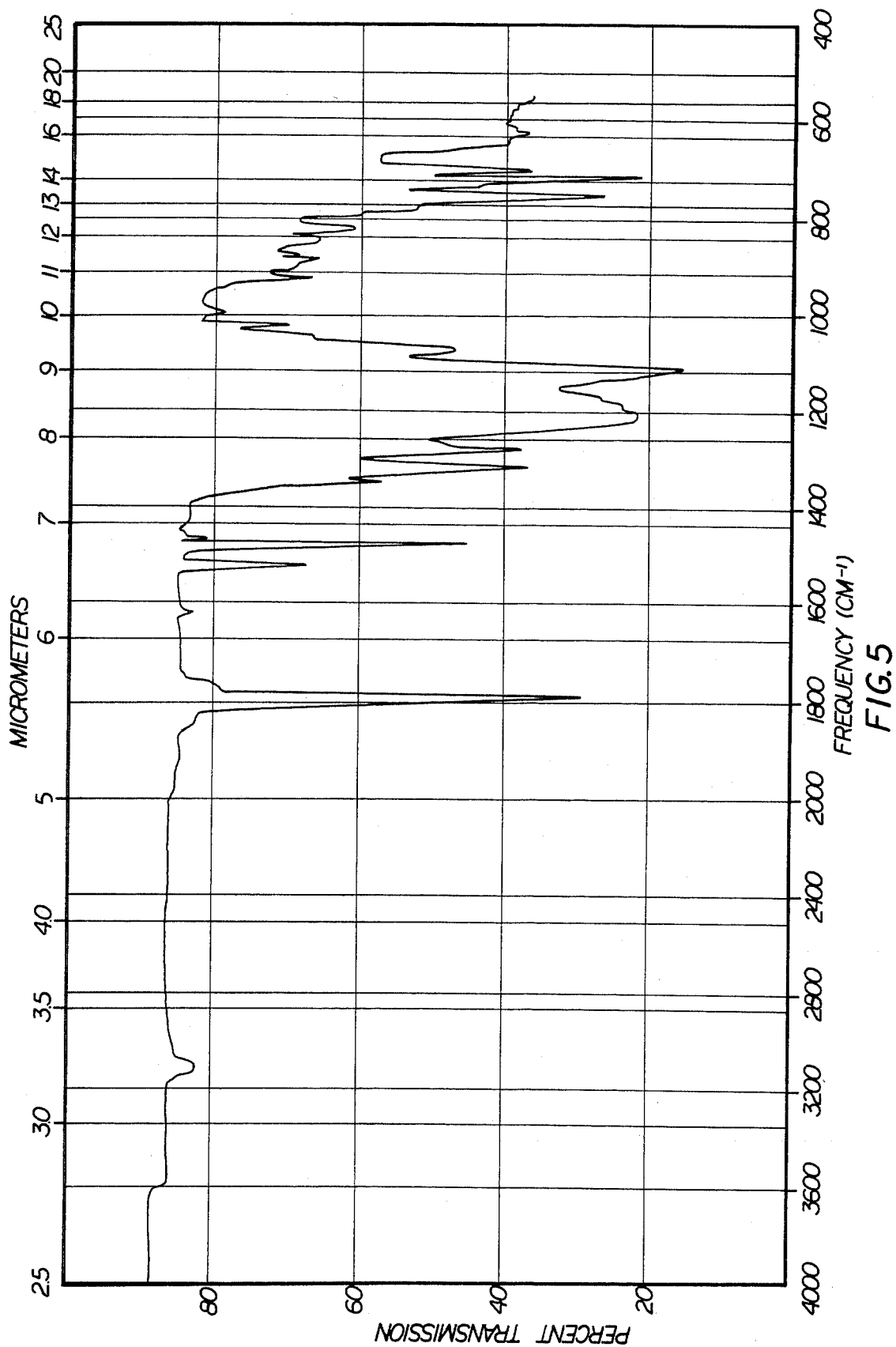
FIG. 5 is a liquid smear scan of the tetrachloro diketone of Example XIa.
Figure 6:
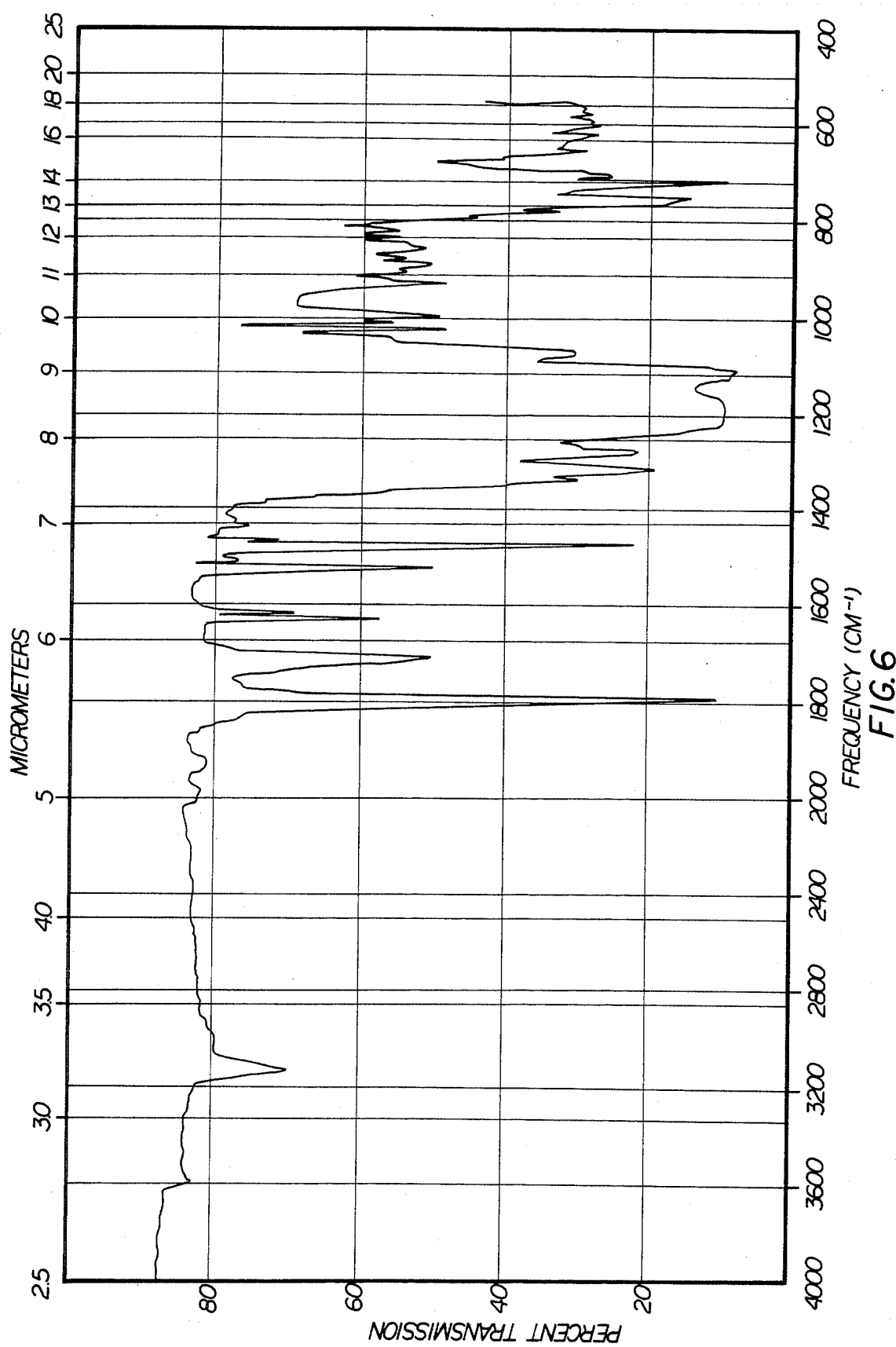
FIG. 6 is a liquid smear scan of the suggested triketone of Example XII.

Two chlorinations of the (HFPO)$_2$ keto-ylid were carried out in a 300-ml autoclave. In the first reaction, 13.2 g of (HFPO)$_2$ keto-ylid was used, while in the second reaction 28 grams were used. The product which was Freon 113 soluble, was collected and determined to contain two components by GLC. The Freon 113 insoluble material, presumably (C$_6$H$_5$)$_3$PCl$_2$, was not fully characterized. The two components were identified by GC/mass spectrometry as isomers of the monochlorinated and dichlorinated products (FIGS. 4, 5, 6). The complications were caused by metal from the reactor leading to Friedel-Craft chlorination of the aromatic ring.

Monochlorinated product

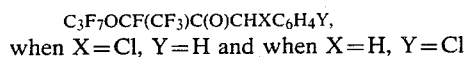

when X=Cl, Y=H and when X=H, Y=Cl

Dichlorinated product

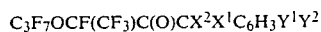

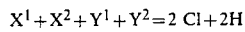

If X$^1$=X$^2$, Y$^1$=Y$^2$
If X$^1$=X$^2$, Y$^1$=Y$^2$

EXAMPLE III

Chlorination of (HFPO)$_2$ Keto-Ylid in Glass

Four chlorination reactions of (HFPO)$_2$ keto-ylid were carried out.

EXAMPLE IIIa

Chlorination of (HFPO)$_2$ Keto-Ylid

A 250-ml, three-necked flask was equipped with a fritted tube, a Dry Ice-acetone condenser, a magnetic stirrer, and a thermowell. The (HFPO)$_2$ keto-ylid (13 g) was added to 150 ml of Freon 113 and chlorine was bubbled in for 30 minutes. The Freon soluble material was collected and the Freon was removed to give eight grams of C$_3$F$_7$OCF(CF$_3$)C(O)CCl$_2$C$_6$H$_5$ having an i.r. scan as shown in FIG. 1 in 83% yield. There was also 16% of the monochloroketone, C$_3$F$_7$OCF(CF$_3$)COCHClC$_6$H$_5$.

EXAMPLE IIIb

Chlorination of (HFPO)$_2$ Keto-Ylid

An ampoule was charged with (HFPO)$_2$ keto-ylid (16.5 g), Freon 113 (30 ml), and chlorine (7.2 g) and heated to 80° C. for one hour. The ampoule was then opened and the products were separated by distillation to give nine grams of the a,a-dichloroketone. This represents a 74% yield.

EXAMPLE IIIc

Chlorination of (HFPO)$_2$ Keto-Ylid

A 250 ml, three-necked flask was equipped with a magnetic stirrer, Dry Ice-acetone condenser, fritted tube, and thermowell and was thoroughly dried. Freon 113 (100 ml) and (HFPO)$_2$ keto-ylid (50 g) were added and chlorine was bubbled in until 0.15 moles had been added. The Freon soluble product was collected (25 ml) and distilled to give the a,a-dichloroketone, C$_3$F$_7$OCF(CF$_3$)C(O)CCl$_2$C$_6$H$_5$, and the monochloro compound, C$_3$F$_7$OCF(CF$_3$)C(O)CHClC$_6$H$_5$, in an 85/15 ratio.

EXAMPLE IIId

Chlorination of (HFPO)$_2$ Keto-Ylid

A 500-ml, three-necked flask was equipped with a magnetic stirrer, thermowell, gas inlet tube, and a Dry Ice-acetone reflux condenser. The (HFPO)$_2$ keto-ylid (100 grams) and Freon 113(200 ml) were added to the flask. The mixture was stirred as an excess of chlorine was added resulting in an exothermic reaction to 50° C. The reaction was complete in five minutes. The Freon solution of a,a-dichloroketone was decanted from the triphenylphosphorous dichloride. Distillation gave the desired dichloroketone (bp 55°–56° C./0.005 mm Hg, 50 grams, 70.2% yield) in 98% purity.

5. Attempted Oxidation of (HFPO)$_2$ Keto-Ylid with Oxygen and Chlorine

The oxidation of (HFPO)$_2$ keto-ylid was attempted using oxygen with 3% chlorine in sunlight. A 250-ml, three-necked flask was equipped with a gas inlet, magnetic stirrer, and condenser. The (HFPO)$_2$ keto-ylid (13 g) was dissolved in 100 ml of Freon 113 and oxygen was bubbled in for 30 minutes before the chlorine addition was begun. After three hours the only product isolated was the a,a-dichloroketone derived from the (HFPO)$_2$ keto-ylid.

6. Addition of Anhydrous HCl to the (HFPO)$_2$ Keto-Ylid

A 250-ml, three-necked flask was equipped with a magnetic stirrer, a bubbler, a Dry Ice-acetone condenser and anhydrous hydrogen chloride was bubbled in. After an excess had been added, there was no Freon soluble product. A water soluble oil was the only produce isolated. This material was tentatively identified as the salt [C$_3$F$_7$OCF(CF$_3$)-C(O)CH(C$_6$H$_5$P+(C$_6$H$_5$)$_3$Cl$^-$].

7. Bromination of (HFPO)$_2$ Keto-Ylid in Freon 113

A 100-ml, three-necked flask was equipped with a magnetic stirrer, additional funnel, thermometer, and condenser. The (HFPO)$_2$ keto-ylid (13.4 g) was dissolved in Freon 113 (50 ml) and an excess of bromine (10 g) was added. There was an immediate precipitation of an oil which was then dissolved in acetonitrile. After removal of the solvents, the thick oily product was collected and infrared analysis indicated the bromine adduct, $C_3F_7OCF(CF_3)C(O)CBr(C_6H_5)P^+(C_6H_5)_3Br^-$.

8. Preparation of (HFPO)$_2$ Acetylene and Addition of Chlorine

The (HFPO)$_2$ derived acetylene was prepared by pyrolyzing the keto-ylid at 200° C. for 16 hours. A sample of the acetylene (2.3 g $C_3F_7OCF(CF_3)CCC_6H_5$) was placed in an ampoule with a two molar excess of chlorine. After heating overnight at 40° C., a GLC indicated the presence of the chlorine adduct, $C_3F_7OCF(CF_3)CCl=CClC_6H_5$, and the tetrachloro adduct, $C_3F_7OCF(CF_3)CCl_2CCl_2C_6H_5$.

9. Attempted hydrolysis of the a,a-Dichloroketone Derived from (HFPO)$_2$ Keto-Ylid A 100-ml Erylenmeyer flask equipped with a magnetic stirrer was used as the a,a-dichloroketone, $C_3F_7OCF(CF_3)C(O)CCl_2C_6H_5$ (4 g), was dissolved in 10 ml of acetone. The mixture was stirred as 3 ml of aqueous ammonium hydroxide was added dropwise. A solid immediately precipitated which was collected and recrystallized from the ethyl ether. Analysis indicated a low fluorine content and nitrogen incorporation in the system. NMR analysis could not establish the identity of the product.

EXAMPLE IVa

Oxidation of (HFPO)$_2$ Keto-Ylid with m-Chloroperbenzoic Acid

A two-liter, three-necked flask was equipped with a magnetic stirrer, dropping funnel, thermometer, and condenser. The (HFPO)$_2$ keto-ylid (50 g) was dissolved in 500 ml of acetone and m-chloroperbenzoic acid (50 g) was added. The mixture was stirred and refluxed for four hours. The solvent was removed and the solid remaining was treated with Freon 113. The solid m-chlorobenzoic acid was removed and the Freon solution distilled to give the a-diketone, $C_3F_7OCF(CF_3)C(O)C(O)C_6H_5$ (5 g).

EXAMPLE IVb

Oxidation of (HFPO)$_2$ Keto-Ylid with m-Chloroperbenzoic Acid

A 50-ml flask was charged with 1 g m-chloroperbenzoic acid, 1 g (HFPO)$_2$ keto-ylid, and 10 ml of reagent acetone. The mixture was heated to reflux for 10 minutes, and after cooling to ambient temperature, 30 ml of Freon 113 was added. The solution was washed with water whereupon solids precipitated out. The lower Freon layer was collected, washed with water, dried over molecular sieves and distilled to give 0.2 g of the desired diketone.

A reaction was repeated on a 10 g scale and worked up without water to give the desired 1,2-diketone. The yield was still ~40%.

EXAMPLE IVc

Preparation of the a-Diketone from a,a-Dichloroketone [$C_3F_7OCF(CF_3)C(O)C(Cl)_2C_6H_5$]

Figure 3:
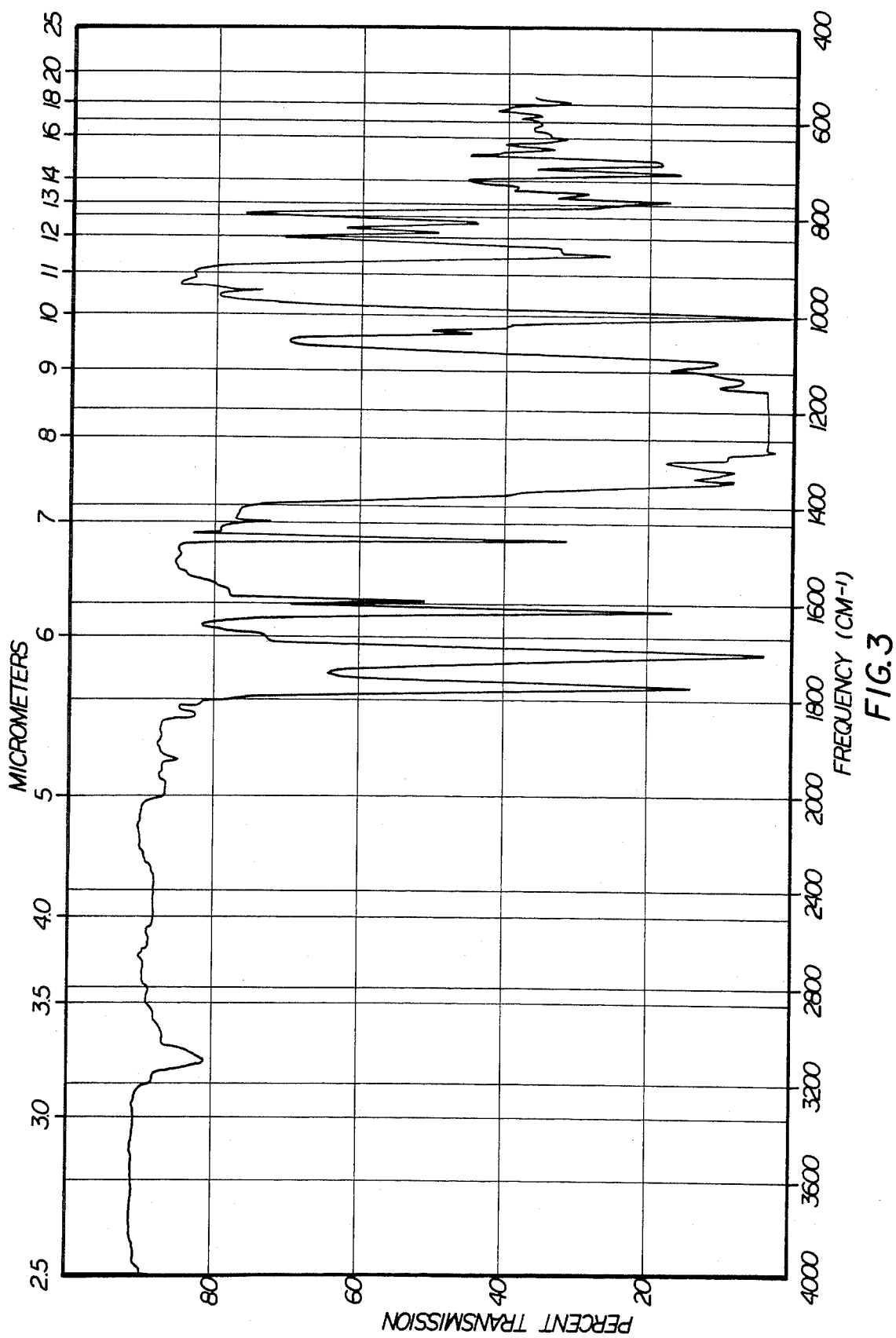
FIG. 3 is a liquid film scan of the product of Example IVc.

A 100-ml, one-necked flask was equipped with a magnetic stirrer and reflux condenser before being charged with acetonitrile (50 ml), silver trifluoroacetate (6.0 g), (HFPO)$_2$ derived a,a-dichloroketone (6.0 g) and water (3 ml). After the mixture had been heated at reflux for 16 hours, a yellow solution containing precipitated silver salts was obtained. The solvents were removed to give the desired diketone (5.5 g) $C_3F_7OCF(CF_3)C(O)C(O)C_6H_5$. This represents a 91% yield of pure a-diketone by GLC (FIG. 3).

EXAMPLE IVd

Preparation of the a-Diketone from a,a-Dichloroketone [$C_3F_7OCF(CF_3)C(O)C(Cl)_2C_6H_5$]

A 500-ml, one necked flask was equipped with a magnetic stirrer, and reflux condenser before being charged with acetonitrile (300 ml), silver trifluoroacetate (44.2 grams) and water (20 ml). The (HFPO)$_2$ derived dichloroketone (40 grams) was added and the mixture was stirred at reflux for 16 hours. After cooling to ambient temperature, the mixture was filtered and the acetonitrile was removed on a rota-evaporator. Freon 113 was added and the a-diketone $C_3F_7OCF(CF_3)C(O)C(O)C_6H_5$, dissolved in the Freon layer which was removed and distilled to give a 100% yield of 95% pure a-diketone.

EXAMPLE V

Preparation of Quinoxaline from (HFPO)$_2$ Derived a-Diketone

Figure 2:
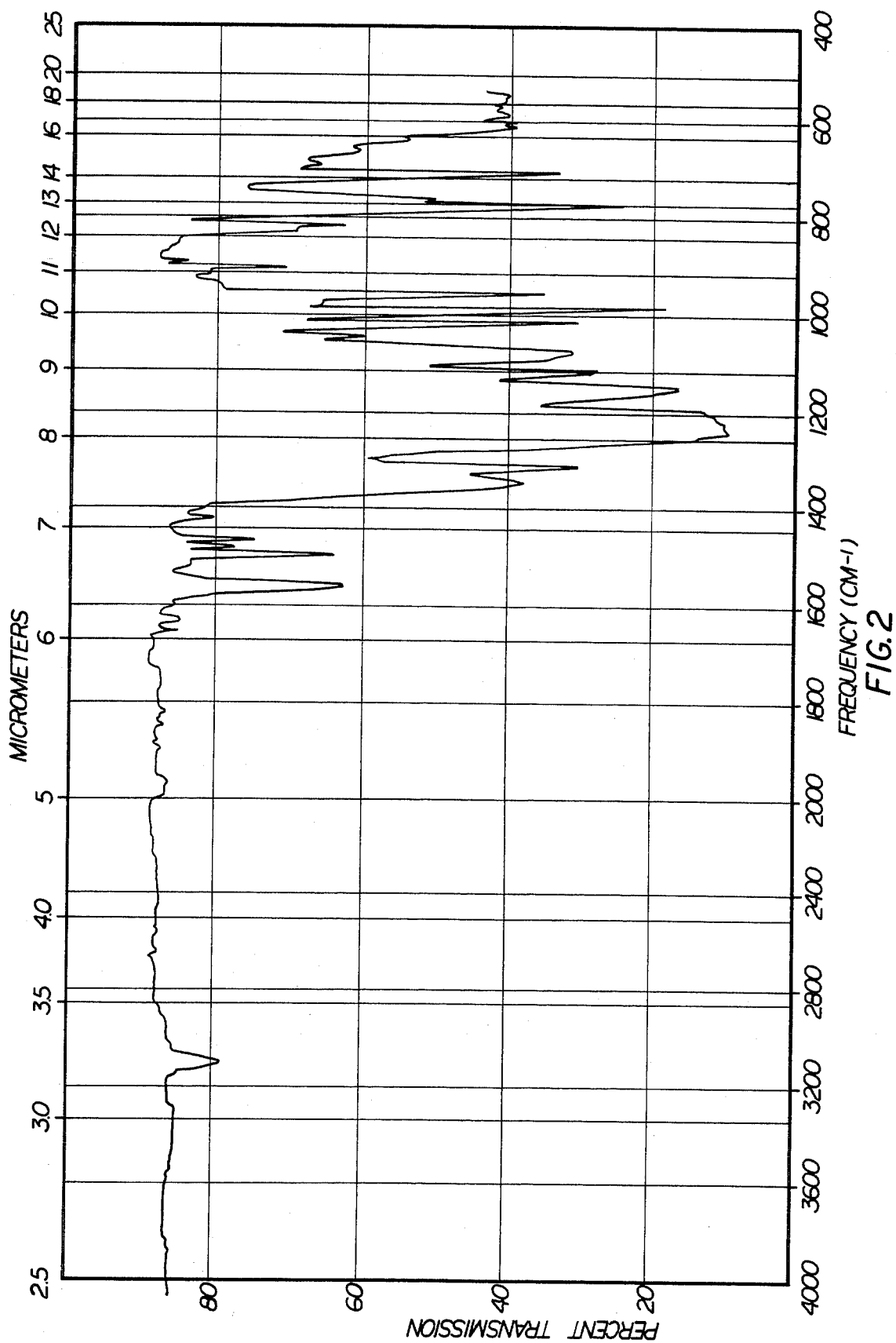
FIG. 2 is a liquid film scan of the quinoxaline of Example V.

A 100-ml, three-necked flask was equipped with a magnetic stirrer, a thermometer, a gas inlet, and a water cooled reflux condenser. The o-phenylenediamine (1.2 g), hexafluoroisopropanol (40 ml) and diketone (5.5 g, $C_3F_7OCF(CF_3)C(O)C(O)C_6H_5$ were added to the flask. There was a slight exotherm to 33° C. and external heat was applied as 1.5 ml of trifluoroacetic acid was added. After refluxing overnight, the solvent was removed and the remaining material was dissolved in Freon 113. After passing through a column of silica then a column of alumina, a water white solution was obtained. Removal of solvent gave the desired quinoxaline (4.2 g) in 78% yield. The quinoxaline was identified by NMR and infrared analysis (FIG. 2).

EXAMPLE Va

Preparation of a Bis-Quinoxaline

A 250-ml, three-necked flask was equipped with a magnetic stirrer, thermowell, dropping funnel, and reflux condenser. Hexa-fluoroisopropanol (100 ml), 3, 4, 3', 4'-tetraaminobiphenyl (2.4 g) and trifluoroacetic acid (0.6 ml) were added to the flask. The (HFPO)$_2$ diketone (8.5 grams) was added dropwise and the mixture was heated to reflux overnight. A TLC indicated two materials which fluoresced in u.v. light. The bis-quinoxaline was isolated by column chromatography to give a white solid product (6.1 grams, 72% yield).

The reaction was repeated using the same amounts of material and freshly recrystallized tetraamine. The reaction was followed by TLC every thirty minutes. The reaction appears to be over within the first two hours, but was still refluxed overnight. The yield was 70% after isolation and purification on a column of alumina and silica gel (FIG. 4).

EXAMPLE VI

Preparation of (HFPO)$_6$ Keto-ylid

A three-liter, three-necked flask was equipped with a magnetic stirrer, thermowell, dropping funnel, and an air cooled reflux condenser leading to a liquid oxygen trap. The system was flushed with dry $N_2$ before being charged with 1.5 liters of diethyl ether and 146 g of benzyltriphenylphosphonium chloride. Butyllithium (318 ml) was added over a two-hour period and the same orange color was again noted. After the reaction mixture was stirred for two hours, the (HFPO)$_6$ acid chloride 195 g, was dropped into the mixture with a change in color to chocolate brown. After the mixture was stirred overnight, it was washed with two liters of water and the ether layers was separated, dried over molecular sieves and evaporated to give the keto-ylid.

EXAMPLE VII

Preparation of (TFEO)$_2$ Diacid Chloride

A two-liter, three-necked flask was equipped with a magnetic stirrer, a gas inlet, a thermowell, and a Vigreaux column followed by a liquid oxygen trap. The 2,3-dichloro-1-oxaperfluorocyclopentene-3 (918 grams) was added to the flask and oxygen with 3% chlorine was bubbled through the solutoin over a two-week period in direct sunlight. The product was collected (806 grams) and distilled to give a precut (146 grams) and ClC(O)CF$_2$OCF$_2$C(O)Cl (546 grams, 65% yield, bp 95°–96° C.

EXAMPLE VIII

Preparation of (TFEO)$_2$ Bis(keto-ylid)

A 12-liter, three-necked flask was equipped with a mechanical stirrer, thermowell, addition funnel and a water cooled condenser. The system was swept with dry nitrogen before the benzyltriphenylphosphonium chloride (780 gram) and ethyl ether (5 liters) were added. Two moles of butyllithium was added to the solution over a one-hour period and the bright orange color indicated reaction. After the mixture was stirred for two hours, the diacid chloride ClC(O)CF$_2$OCF$_2$C(O)Cl (122 grams) was added via the dropping funnel. The bright orange color was discharged by addition of the acid chloride giving a light tan slurry. The solids were removed by filtration and no bis(keto-ylid) was isolated from the ether solution. The remaining solids were extracted with hot acetone which separated the bis(keto-ylid) from the benzyltriphenylphosphonium chloride and lithium chloride. A total of 340 grams of the bis(keto-ylid) was collected representing an 80% yield.

EXAMPLE IX

Purification of (TFEO)$_2$ Bis(keto-ylid)

The impurities found in the (TFEO)$_2$ bis(keto-ylid) (Example VIII) were removed by heating the solid at 125° C. for 16 hours at full vacuum.

EXAMPLE X

Chlorination of (TFEO)$_2$ Bis(keto-ylid)

A 250-ml, three-necked flask was equipped with a magnetic stirrer, thermometer, Dry Ice-acetone condenser, and gas inlet. The bis(keto-ylid) was not soluble in Freon but formed a suspension. Chlorine (excess) was added, allowed to reflux and vented. Work-up revealed that the chlorination was incomplete; however, ca. two grams of crude tetrachlorodiketone were isolated.

EXAMPLE Xa

Chlorination of (TFEO)$_2$ Bis(Keto-ylid)

The chlorination was repeated in a 500-ml Fischer-Porter bottle using chlorine as a solvent for the reaction. The bis(keto-ylid) (21 grams) was placed in the bottle, cooled to liquid oxygen temperature and the bottle evacuated to full vacuum. The chlorine (50 grams) was condensed into the bottle and warmed to −78° C. in a Dry Ice-acetone bath for one hour. The system was then warmed to 0° C. and further to ambient temperature overnight. The following morning the excess chlorine was vented and the bottle evacuated to give a clear slightly yellow oil. The contents were washed from the bottle with methylene chloride and extracted with Freon 113 to give the product (10 g). Distillation gave a low boiling product (bp 30° C./3 mm) which has not been identified but may be a mixture of chlorinated acetones. The bis(keto-ylid) was analyzied by NMR and was shown to contain acetone as an impurity. The residue was chromatographed on silica gel and alumina to give a clear product.

EXAMPLE XI

Preparation of the Tetrachlorodiketone from (TFEO)$_2$ Bis(keto-ylid)

A 250-ml, three-neck flask was equipped with a magnetic stirrer, a gas inlet tube, a Dry Ice-acetone condenser, and a thermowell. The (TFEO)$_2$ bis(keto-ylid) (21 g) was slurried in 100-ml of carbon tetrachloride. Chlorine (10 g) was added as the temperature rose to 56° C. and the keto-ylid went into solution leaving a thick oil in top of the solution. The carbon tetrachloride solution was decanted, the CCl$_4$ removed and the residue dissolved in Freon 113. This material was passed through a column of silica gel to give six grams of Freon 113 soluble material which was shown to consist of two components by TLC. Mass spectral analysis was inconclusive but suggested the triketone hydrate, $C_6H_5CCl_2C(O)CF_2OCF_2C(O)C_6H_5$—$H_2O$, had been formed. The oil, which was Freon 113 insoluble, solidified on standing and gave triphenylphosphine oxide on work up.

EXAMPLE XI(a)

Preparation of the Tetrachlorodiketone from (TFEO)$_2$ Bis(Keto-ylid)

The chlorination was repeated using great caution to remove any water from the reaction. The (TFEO)$_2$ bis(keto-ylid) (20 g) was dried at 120° C. under full vaccum, the chlorine (10 g) was passed through 5A molecular sieves and the entire system was dried and flushed with dry nitrogen during the reaction. As the chlorine was added, there was again an exotherm to 56° C. which subsided as an excess of chlorine was added. The carbon tetrachloride solution was again decanted and the solvent removed to give 9.2 g of yellow oil. Mass spectral analysis indicated the product to be the desired tetrachlorodiketone, $C_6H_5CCl_2C(O)CF_2OCF_2C(O)CCl_2C_5H_5$ (FIG. 5).

A large scale chlorination was carried out on the (TFEO)$_2$ bis(keto-ylid) (50 g). An exotherm to 65° C. was noted and the products were worked-up as in the previous reactions. Removal of the carbon tetrachloride gave 23 g of yellow oil which was identical to the tetrachlorodiketone isolated in the small scale experiment.

EXAMPLE XX

Preparation of (TFEO)$_8$ Derived Polyquinoxaline with 3,3'-Diaminobenzidine

A 100-ml, three necked flask was equipped with a magnetic stirrer, heating mantle, thermometer, addition funnel and condenser. The 3,3'-diaminobenzidine was recrystallized from methanol before being added (0.857 grams) to the hexafluoroisopropanol (50 ml). The (TFEO)$_8$ tetraketone (4.35 grams) and 1 ml of trifluoroacetic acid as a catalyst were added. The reaction exothermed to 27° C. and was then heated at reflux for 16 hours. Work-up was accomplished by removing the hexafluoroisopropanol and trifluoroacetic acid before dissolving the thick material in Freon 113. After passing the solution through a column of alumina, a tan solid was collected upon removal of the solvent.

EXAMPLE XXI

Conversion of (TFEO)$_4$ Diacid Fluoride to the Desired (TFEO)$_4$Diacid Chloride A 250-ml polyethylene Erylenmeyer flask was equipped with a magnetic stirrer before the (TFEO)$_4$ diacid fluoride was added (114 grams). The deionized water (150 ml) was added slowly and the material stirred for 16 hours.

The (TFEO)$_4$ diacid was salted out of the water with excess sodium chloride and was then dried over molecular sieves. A 250-ml, three-necked flask was equipped with a magnetic stirrer, a thermometer, dropping funnel, and a condenser before the crude diacid was added (136 grams). The thionyl chloride (75 ml) was added via a dropping funnel after 1 ml of pyridine had been added. After four hours at reflux the lower layer of (TFEO)$_4$ diacid chloride was isolated and distilled to give the desired product, $ClC(O)(CF_2OCF_2)_3C(O)Cl$, (91 grams, 95 percent yield).

EXAMPLE XXII

Preparation of (TFEO)$_4$ Derived Bis(keto-ylid)

A three-liter, three-necked flask was equipped with a mechanical stirrer, cooling bath, thermowell, dropping funnel and a condenser. The benzyl triphenylphosphonium chloride (194 grams, 0.5 mole) was added to 1.5 liters of ethyl ether and slurried before the n-butyllithism (0.5 moles) was added. There was an immediate color change to bright orange. After allowing the mixture to stir for one hour the (TFEO)$_4$ diacid chloride (45 grams, 0.125 moles) was added via the dropping funnel. The immediate color change to light tan as the last of the diacid chloride was added indicated the reaction was complete. After stirring overnight, the materials were filtered and the solids washed repeatedly with hot acetone. The acetone was removed on a rota-evaporator to give a pink solid which was recrystallized from acetone to give the desired bis(keto-ylid) (91 grams, 73 percent yield).

EXAMPLE XXIII

Preparation of (TFEO)$_4$ Derived Tetrachlorodiketone

A 1-liter, three-necked flask was equipped with a mechanical stirrer, thermowell, gas inlet tube, and a Dry Ice cooled condenser. The (TFEO)$_4$ derived bis(keto-ylid) (84 grams) was added to 500 ml of Freon 113 and chlorine addition was begun. After an initial exotherm to 30° C., the refluxing chlorine cooled the reaction mixture to 0° C. and the chlorine addition was terminated. The excess chlorine was allowed to vent overnight and a yellow oil was separated from the Freon 113 layer. The Freon 113 layer contained none of the tetrachlorodiketone and the yellow oil was dissolved in methylene chloride (200 ml). Work up by washing the methylene chloride solution with hot water, drying, and passing the solution through a column of alumina and silica gave 36 grams of the tetrachlorodiketone and dichlorotriketone mixture for a 69 percent yield.

EXAMPLE XXIV

Preparation of TFEO

Tetrafluoroethylene oxide was prepared by the reaction of tetrafluoroethylene and oxygen with bromine as initiator. The product was purified by scrubbing out the TFE and by-products and analyzed by IR spectroscopy. The reactor produced approximately 150 g of TFEO per full day of operation; a total of 1,000 grams was collected and stored in a stainless steel cylinder at $-78°$ C.

EXAMPLE XXV

Hydrolysis of (TFEO)$_{7-10}$ Diacid Fluoride

A previously prepared sample of the diacid fluoride (32 grams) was placed in a 250 ml polyethylene flask and stirred as deionized water was added. Excess water was decanted off, the waxy solid collected and stored in vacuo to give 29.0 grams of the (TFEO)$_{7-10}$ diacid.

EXAMPLE XXVI

Preparation of (TFEO)$_{7-10}$ Diacid Chloride

A 100-ml, three-necked flask was fitted with a magnetic stirrer, thermowell, condenser and backed by a liquid oxygen trap. The (TFEO)$_{7-10}$ diacid (29 grams) along with 30 ml thionyl chloride and 1.5 ml pyridine were added and the mixture heated to reflux for one hour. The solution was cooled, transferred to a separatory funnel and the lower layer separated to give 29.0 grams of the (TFEO)$_{7-10}$ diacid chloride.

EXAMPLE XXVII

Reaction of (TFEO)$_{7-10}$ Diacid Chloride with $\phi_3P=CHC_6F_5$

A 500-ml, three-necked flask was equipped with a magnetic stirrer, thermowell, water-cooled condenser, a pressure equalized dropping funnel, and a gas outlet leading to a nitrogen by-pass and through a bubbler. The flask was charged with pentafluorobenzyltriphenylphosphonium bromide (11.77 g, 0.225 mole), ethyl ether (150 ml) and flushed with nitrogen before the n-butyllithium (0.225 mole) was added over 30 minutes. A yellow/gold color indicated reaction.

The mixture was stirred for a further hour before the (TFEO)$_{7-10}$ diacid chloride (10.0 g, ~0.009 mole) was added over 20 minutes. After addition, the solution turned base white and was stirred overnight. The solution was pressure filtered through a celite plug, the solid residue being washed copiously with ether. The solvent was partially removed and 6.0 g. of Sigel (70-230 mesh) added; the remainder of the solvent was removed. The solid material was placed on a 10 cm $\times$ 2 cm Sigel/Et$_2$O column and eluted with H$_2$O. Removal of the solvent gave a white waxy solid. "Sigel" is a silica gel.

EXAMPLE XII

Preparation of the Tetraketone from (TFEO)$_2$ Tetrachlorodiketone

A 250-ml, one-neck flask was equipped with a magnetic stirrer, thermowell, and reflux condenser. The (TFEO)$_2$ derived tetrachlorodiketone (6 grams) was added to 100 ml of acetonitrile, silver trifluoroacetate (10.74 g) and water (1 g). The mixture was refluxed for six hours before the acetonitrile was filtered and the carbon tetrachloride removed to give 3 grams of yellow oil. Mass spectra analysis suggested the triketone, $C_6H_5CCl_2C(O)CF_2OCF_2C(O)C(O)C_6H_5$, to be the major constituent. (FIG. 6). This material would not yield the desired polymer due to insufficient functionality.

EXAMPLE XIII

Preparation of (TFEO)$_4$ Acid Chloride

A one-liter, three-neck flask was equipped with a magnetic stirrer, dropping funnel, thermowell, and condenser. Sodium hydroxide (11 g) and water (230 ml) were added to the flask and stirred as the $C_2F_5O(CF_2CF_2O)_2CF_2COOMe$ (126 g) was added via the dropping funnel. Freon 113 (250 ml) was added with aqueous HCl (50 ml). The Freon layer was isolated, dried over molecular sieves and evaporated to give 106 g of acid, $C_2F_5O(CF_2CF_2O)_2CF_2COOH$. This material was added to a 250-ml flask with 5 cc of pyridine.

Thionyl chloride was then added over a one hour period. After the mixture was refluxed, cooled and filtered, the acid chloride was isolated and distilled to give 56 g of (TFEO)$_4$ acid chloride.

EXAMPLE XIV

Preparation of (TFEO)$_4$ Derived Keto-Ylid

A two-liter, three-necked flask was equipped with a magnetic stirrer, thermowell, dropping funnel, and an air cooled reflux condenser leading to a liquid oxygen trap. After flushing with dry $N_2$, one-liter of diethyl ether and 78 g of benzyltriphenylphosphonium chloride were added. Butyllithium (152 ml, 0.2 moles) was added dropwise and an orange color developed immediately. After the addition, the mixture was stirred for two hours before the $CF_3CF_2O(CF_2CF_2O)_2CF_2O)_2CF_2COCl$ (48 g, 0.1 moles) was added. After one hour of stirring, the mixture was filtered through a pressure filter and the ether was removed to give the desired keto-ylid.

EXAMPLE XV

Pyrolysis of

$$CF_3CF_2O(CF_2CF_2O)_2\overset{\overset{O}{\|}}{C}C(C_4H_6){=}P(C_6H_5)_3$$

The keto-ylid prepared in Example VIII above was placed in a 100-ml flask equipped with a distillation head and heated. The temperature quickly reached 260° C. which caused decomposition of the keto-ylid to an acid fluoride. There was a small amount ~1 g of an acetylene compound collected which was passed through neutral alumina.

EXAMPLE XVI

Preparation of $ClCO(CF_2OCF_2)_5COCl$

A Nalgene, 125-ml flask was used to hydrolyze 100 grams of (TFEO)$_6$ diacid fluoride to the diacid with deionized water. The white solid was collected and placed in a 250-ml, three-necked flask which was equipped with a magnetic stirrer, dropping funnel, thermowell, and condenser. Pyridine (2 ml) was added and thionyl chloride (100 ml) was added via the dropping funnel. After the addition was complete, the mixture was refluxed for three hours. The product was phase separated and the product was isolated to give 91 g (83%) of the diacid chloride. This material was used to prepare the bis(keto-ylid).

EXAMPLE XVII

Preparation of (TFEO)$_6$ Bis(Keto-Ylid)

A three-liter, three-necked flask was equipped as in previous reactions and a dry nitrogen sweep used to sweep the flask before 650 ml of dry diethyl ether and (75 g) of benzyltriphenylphosphonium chloride were added. Butyllithium (0.38 moles) was added dropwise and the mixture was stirred for ½ hour before the diacid chloride [(TFEO)$_6$] (91 g, 0.11 moles) was added via the dropping funnel. After stirring overnight, the solids were filtered out and the ether removed to leave a viscous oil which was dissolved in Freon 113 and passed through a column of alumina. The product, bis(keto-ylid) (41 g, 26% yield) was then isolated. It was later found that the product was sparingly soluble in diethyl ether, a fact which explains the surprisingly low isolated yield in this reaction.

EXAMPLE XVIII

Chlorination of (TFEO)$_8$ Derived Bis(keto-ylid)

The chlorination of (TFEO)$_8$ bis(keto-ylid) in Freon 113 was carried out using chlorine in a dry system. Workup included air drying of the resulting oil and redissolving the semi-solid in Freon 113 before passing the solution through a column of silica gel and alumina. A total of 25 grams of (TFEO)$_8$ bis(keto-ylid) was chlorinated in a three-necked 250 ml flask equipped with a magnetic stirrer, gas inlet tube, thermometer and Dry Ice condenser. The Freon 113, 100 ml, was added to the bis(keto-ylid) and chlorine was added over a 30 minute period. Work-up gave 16 grams, 72 percent yield, of a mixture of the dichlorotriketone, $C_6H_5CCl_2C(O)(CF_2OCF_2)_7C(O)C(O)C_6H_5$, and tetradichlorodiketone.

EXAMPLE XIX

Preparation of (TFEO)$_8$ Tetraketone

Hydrolysis of the (TFEO)$_8$ chloroketone of Example XVIII with silver trifluoroacetate was carried out in a 200 ml, one-necked flask equipped with a magnetic stirrer and a condenser. The acetonitrile (60 ml), silver trifluoroacetate (9.6 grams) and chloroketone were refluxed for 20 hours before the silver salts were removed by filtration. Removal of the acetonitrile gave a bright yellow oil which was dissolved in 30 ml of Freon 113 and passed through a column of alumina to remove the acidic impurities. The tetraketone, $C_6H_5C(O)C(O)(CF_2OCF_2)_7C(O)C(O)C_6H_5$, was collected in 75 percent yield.

The (TFEO)$_{7-10}$ diacid chloride was similarly reacted with methyl, ethyl, benzyl triphenylphosphonium bromides or chlorides in a similar manner.

EXAMPLE XXVIII

Synthesis of

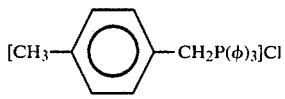

A flask was charged with toluene (3 liter) triphenylphosphine (745 g, 2.84 mole), and p-methylbenzyl chloride (200 g, 1.42 mole). This mixture was stirred at reflux for eight hours. The mixture was then cooled and filtered and the precipitate was washed with 2×1300 ml of toluene. The tan, solid product was dried in a vacuum desiccator to give 310 g (54% yield) of the dried salt.

EXAMPLE XXIX

Synthesis of Bis(keto-ylid) of (TFEO)$_{7-10}$ diacid Cl

Following earlier described procedures, 72.8 g (187 mole) of [$\phi$CH$_2$P($\phi$)$_3$]Cl was converted to $\phi$CH=P($\phi$)$_3$ which was then reacted with 44 g (46.8 mmole) of ClC(O)(CF$_2$OCF$_2$)$_7$C(O)Cl in ethyl ether. The reaction mixture was filtered and the ether was removed from the filtrate to leave a brown semi-solid. This material was redissolved in 100 ml of ether, treated with 10 g of triethylamine, and filtered. The filtrate was evaporated to dryness to again leave a brown semi-solid.

The semi-solid was again dissolved in ethyl ether and this solution was passed through a column of silica gel. Evaporation of solvent left 50 g (74% yield) of brown semi-solid. NMR analysis confirmed that this material was the desired keto-ylid.

EXAMPLE XXX

Synthesis of Perfluoro Oxyglutaryl Chloride

A three-liter autoclave was charged with dichloromaleic anhydride (1,005 g, 6.02 mole) and sulfur tetrafluoride (913 g, 8.45 mole) and heated at 190° for 48 hours. It was then cooled to room temperature and the volatiles were removed to slightly below atmospheric pressure.

The autoclave was then charged with an additional 902 g (8.35 mole) of sulfur tetrafluoride and 107 g (5.35 mole) of anhydrous hydrogen fluoride and heated at 190° for an additional 120 hours. After cooling to room temperature the overgas was removed before the autoclave was opened to produce 1,238 g of liquid product. This material was washed with 5% KOH and then dried over Molecular Sieves to leave 990 g of material which GC indicated was 78%

The above material was reacted with oxygen containing a trace of chlorine in the presence of u.v. light to produce 646 g of the crude ClC(O)CF$_2$OCF$_2$C(O)Cl.

The autoclave reaction was repeated to produce an additional 1,052 g of

(81% by GC). This material was oxidized to produce 713 g of ClC(O)CF$_2$OCF$_2$C(O)Cl.

Both samples of crude oxyglutaryl chloride were combined and distilled to produce 750 g of the pure diacid chloride.

EXAMPLE XXXI

Preparation of (TFEO)$_{7-9}$ Keto-Ylid

A three-liter flask was equipped with a mechanical stirrer, thermometer, 0° reflux condenser vented to a −78° trap, and an addition funnel containing n-butyllithium (136 g, 340 mmole). The flask was charged with ethyl ether (1.2 liters) and benzyltriphenylphosphonium chloride (133 g, 340 mmole). This solution was stirred as the n-butyllithium was added dropwise. A bright orange color was immediately apparent. The reaction mixture was stirred for one hour and then C(O)Cl(CF$_2$OCF$_2$)$_{7-9}$C(O)Cl (81g, ∼77 mmole) was added dropwise until the color changed to bone white. Work up with ethyl acetate gave ∼76% yield of a mixture of the corresponding keto-ylids.

EXAMPLE XXXII

Preparation of (TFEO)$_{7-9}$ Perfluorobenzyl Keto-ylid

A three-liter flask equipped with a mechanical stirrer, thermometer, 0° reflux condenser, and addition funnel was charged with ethyl ether (1 liter) and pentafluorobenzyltriphenylphosphonium bromide (179 g, 342 mmole). The solution was stirred as n-butyllithium (342 mmole) was added via the addition funnel. A color change to bright gold was noted.

The reaction mixture was stirred for one hour and then ClC(O)(CF$_2$OCF$_2$)$_{7-9}$C(O)Cl (70 g, ∼66 mmole) was added dropwise until the color of the reaction mixture changed to light tan. The reaction mixture was filtered and the filtrate was evaporated to leave the crude bis(keto-ylid). This material was recrystallized from ethyl acetate, washed with hexane, and dried to give a 78% yield of $\phi_3$P=C(C$_6$F$_5$)C(O)(CF$_2$OCF$_2$)$_{7-9}$C(O)C(C$_6$F$_5$)=P$\phi_3$.

EXAMPLE XXXIII

Chlorination of (TFEO)$_{7-9}$ Perfluorobenzyl keto-ylid

A 500-ml flask containing a stirring bar was equipped with a thermometer, −78° reflux condenser, and a gas inlet tube containing 5A molecular sieves and calcium sulfate. The flask was charged with methylene chloride (200 ml) and $\phi_3$P=C(C$_6$F$_5$)C(O)(CF$_2$OCF$_2$)$_3$C(O)ClC$_6$F$_5$)=P$\phi_3$ (31 g, 24 mmole) and this solution was stirred as chlorine (20 g, 280 mmole) was admitted via the gas inlet tube. A slight exotherm to 38° was noted.

Figure 7:
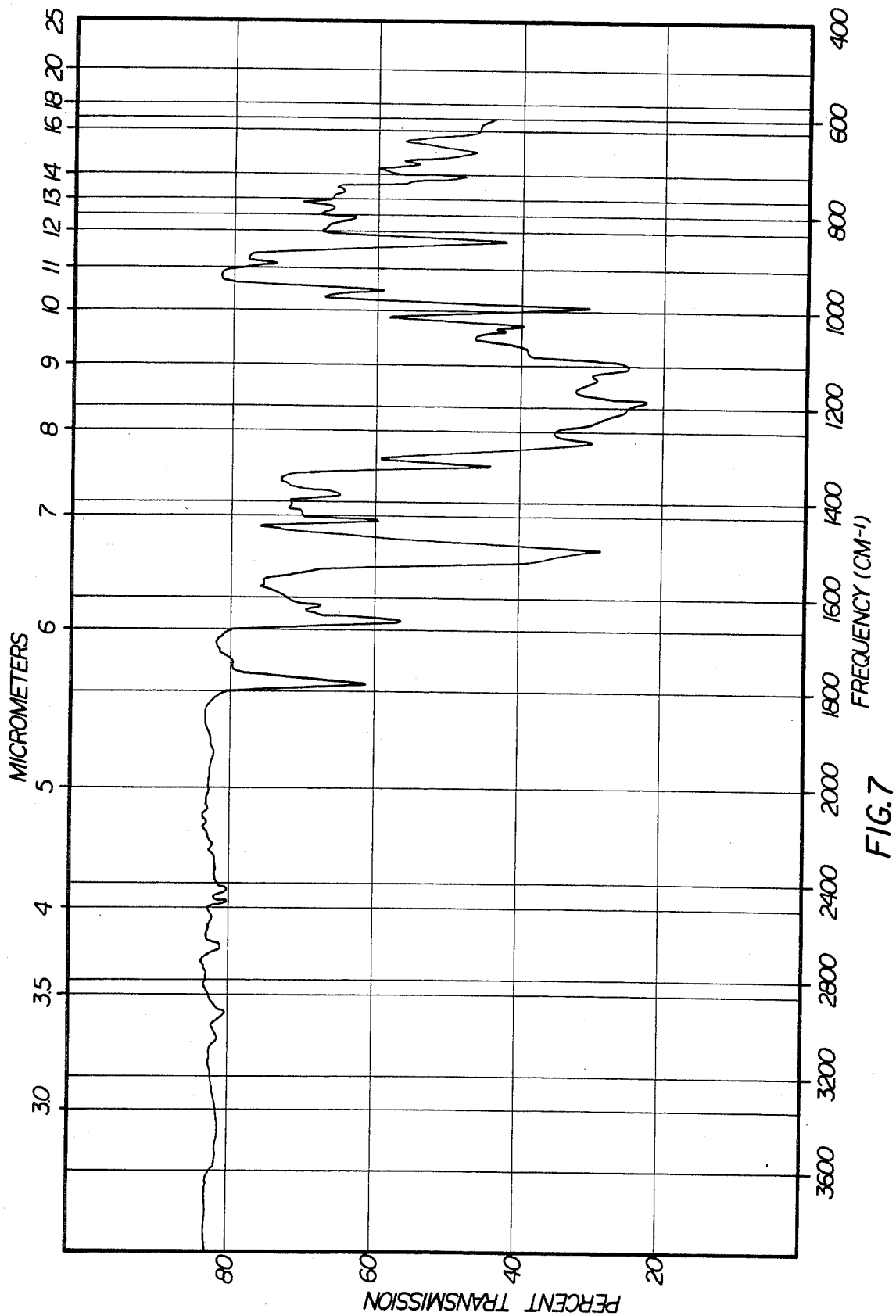
FIG. 7 is a liquid smear scan of the product of Example XXXIII.

The excess chlorine was vented and the methylene chloride was removed to leave an oil which was dissolved in Freon 113. The Freon solution was passed through a column of alumina after which the Freon was removed to leave a mixture of C$_6$F$_5$CCl$_2$C(O)(CF$_2$OCF$_2$)$_3$C(O)CCl$_2$C$_6$F$_5$ and C$_6$F$_5$CCl$_2$C(O)(CF$_2$OCF$_2$)$_3$C(O)C(O)C$_6$F$_5$; infrared spectrum, FIG. 7.

EXAMPLE XXXIV

Chlorination of (TFEO)$_{7-9}$ Keto-ylid

A 500-ml flask was equipped with a magnetic stirring bar, thermometer, gas inlet, and −78° reflux condenser and flushed with dry nitrogen. The flask was then charged with Freon 113 (200 ml) and the title compound (40 g, ~240 mmole). This mixture was stirred as chlorine (20 g, 280 mmole) was bubbled beneath the surface of the liquid. An exotherm to 43° indicated reaction. The reaction mixture was stirred for four hours after which the excess chlorine was vented.

Work-up through a column of silica and alumina produced a mixture of the tetrachlorodiketone and dichlorotriketone in 70% yield.

EXAMPLE XXXV

Chlorination of (TFEO)$_{7-9}$ Perfluorobenzyl keto-ylid

A 500-ml flask containing a magnetic stirring bar was equipped with a thermometer, gas inlet, and −78° reflux condenser and charged with Freon 113 (200 ml) and $\phi_3P=C(C_6F_6)C(O)(CF_2OCF_2)_{7-9}C(O)C(C_6F_5)=P\phi_3$ (30 g, ~16 mmole). The reaction mixture was stirred as chlorine (19 g, 270 mmole) was bubbled under the surface. After all the chlorine had been added, an infrared spectrum of the reaction mixture indicated that some keto-ylid remained. Stirring in the presence of chlorine was continued for 16 hours. Work-up through a column of alumina and silica gel gave a slightly yellow oil (20 g) which was shown by mass spectral analysis to be a mixture of the tetrachlorodiketone and dichlorotriketone.

The above reaction was repeated using 97 g of the bis(keto-ylid) and 32 g of chlorine in 230 ml of Freon 113 to give an additional quantity of the chloroketone mixtures.

EXAMPLE XXXVI

Preparation of (TFEO)$_{8-10}$ Acid Fluoride

A one-liter flask containing a magnetic stirring bar was charged with cesium fluoride (15 g) and fitted with a stopcock adapter. The flask was connected to a vacuum manifold and heated at 180° for 16 hours. It was then cooled to ambient temperature and charged with tetraglyme (250 ml). This was followed by cooling to 0° and the subsequent addition of $FC(O)(CF_2OCF_2)_4C(O)F$ (202 g, 0.362 mole).

The overgases were removed and the addition of

TFEO was started. After 16 hours, 45 g (0.39 mole) of TFEO had been added at 0°. At this point an infrared spectrum of the contents of the TFEO cylinder indicated that most of the material had rearranged to trifluoroacetyl fluoride.

A new cylinder was connected to the vacuum manifold and 225 g (1.94 mole) of TFEO was added at 0° during a 32-hour period. After this addition the reaction was terminated and the product mixture was treated with sulfur dioxide. The acid fluorides were separated from the tetraglyme and heated at 60° C. under full vacuum to remove lower molecular weight oligomers. This left 314 g of $FC(O)(CF_2OCF_2)_nC(O)F$ where n=8–10.

EXAMPLE XXXVII

Preparation of Pentafluorobenzyltriphenylphosphonium Bromide

A five-liter, three-necked flask equipped with a mechanical stirrer, reflux condenser, and thermometer was charged with toluene (3.3 liters), triphenylphosphine (686 g, 2.62 mole), and pentafluorobenzyl bromide (343 g, 1.31 mole). The contents were stirred and heated slowly to reflux. A white precipitate formed as the reaction progressed. At the completion of the reaction the flask was cooled to ambient temperature and the solid product was filtered and washed with hot toluene (2.6 liters). These solids were dried in a vacuum desiccator to give a 90% yield of pentafluorobenzyltriphenylphosphonium bromide.

EXAMPLE XXXVIII

Preparation of (TFEO)$_3$ pentafluorobenzyl bis-keto-ylid

A one-liter flask equipped with a mechanical stirrer, addition funnel, thermometer, and 0° condenser was purged with nitrogen and charged with pentafluorobenzyltriphenylphosphonium bromide (90 g, 0.17 mole) and ethyl ether (300 ml). The solution was stirred as n-butyllithium in hexane (68 grams) was added dropwise until the color of the reaction mixture changed to bright orange. The reaction mixture was stirred for one hour and then $ClC(O)(CF_2OCF_2)_3C(O)Cl$ (20 g, 0.042 mole) was added dropwise until a titration end point was reached as indicated by the color change in the solution.

The resulting tan slurry was filtered and the solids were recrystallized from acetone to yield 45 grams (67% yield) of brown product. A second recrystallization produced 23 g of white bis(keto-ylid).

EXAMPLE XXXIX

Chlorination of (TFEO)$_3$bis(keto-ylid)

A 500-ml flask was charged with methylene chloride (100 ml) and $\phi_3P=C(\phi)C(O)(CF_2OCF_2)_3C(O)C(\phi)=P\phi_3$ (51 g, 0.046 mole). Chlorine gas (20 g, 0.28 mole) was passed through 5A molecular sieves to remove traces of HCl and then bubbled into the solution of bis(keto-ylid). Work-up of the product mixture produced 29 g of material. This crude product was dissolved in a solution of Freon 113 and methylene chloride and passed through a column of alumina. Evaporation of the solvent left 26 g of a light yellow oil which showed two spots by TLC. Analysis by NMR showed that the product was 75/25 $\phi CCl_2C(O)(CF_2OCF_2)_3C(O)CCl_2\phi / \phi CCl_2C(O)(CF_2OCF_2)_3C(O)\,C(O)\phi$.

EXAMPLE XL

Preparation of TFEO

Tetrafluoroethylene oxide was prepared over a ten-day period using tetrafluoroethylene, oxygen, and bromine as an initiator. The reaction gave an average yield of 84 grams per day. Analysis by infrared, showed the product to be the desired epoxide after scrubbing out the unreacted tetrafluoroethylene and by-products. A total of 840 grams of pure product was collected and stored in a stainless steel cylinder at −78° C.

EXAMPLE XLI

Preparation of F-Oxyglutaryl Fluoride

A three-liter, three-necked flask was euipped with a mechanical stirrer, thermometer, addition funnel, and a Vigreaux column topped by an ice-water cooled distillation head. The flask was charged with potassium fluoride (285 grams) and heated to 190° C. as a full vacuum was applied over a 16-hour period. After cooling the system to room temperature, diethylene glycol dimethyl ether (1.5 liters) was added and the mixture heated to 125° C. with stirring. The F-oxyglutaryl chloride (350 grams) was added over a 1.25-hour period with the product being distilled out as it was prepared. Further distillation on a 25-plate Oldershaw column gave 247 grams of pure F-oxyglutaryl fluoride in 82% yield.

EXAMPLE XLII

Preparation of (TFEO)$_n$ Oligomers

A three-liter, three-necked flask was equipped with a thermometer well, a septum, a gas inlet and a magnetic stirrer. The cesium fluoride (15 grams) was placed in the flask and a full vacuum applied as the flask was heated to 180° C. overnight. The following morning the flask was cooled to ambient temperature and the heating mantle replaced with a cooling bath. Tetraglyme (500 ml), tetraethylene glycol dimethyl ether, was added along with the F-oxyglutaryl fluoride (247 grams). The flask was cooled to −78° C., evacuated, then allowed to warm to 0° C. before addition of TFEO through a manifold was begun. The temperature was maintained at 0°±5° C. until 410 grams of TFEO had been added. The reaction was then terminated as SO$_2$ was bubbled through the mixture. Separation of the lower fluorocarbon layer gave 571 grams of crude oligomers which were analyzed by GLC to show (TFEO)$_n$ where n=4, 5, and 6.

Still other higher oligomers may be prepared according to this procedure or those described in U.S. Pat. No. 3,250,806 supra.

EXAMPLE XLIII

Hydrolysis of (TFEO)$_n$ Diacid Fluoride

The (TFEO)$_8$ diacid fluoride (98 grams) was placed in a 250-ml polyethylene flask and stirred as deionized water was added. The waxy white solid was collected, dried under full vacuum to give 93 grams of (TFEO)$_8$ diacid, a 95% yield.

EXAMPLE XLIV

Preparation of (TFEO)$_8$ Diacid Chloride

A 250-ml, three-necked flask was equipped with a magnetic stirrer, thermowell, condenser and backed by a dry ice-acetone cooled trap. The (TFEO)$_8$ diacid (93 grams) along with 100 ml thionyl chloride and 4 ml pyridine were added and the mixture heated. After the evolution of HCl and SO$_2$ had stopped, the mixture was cooled from 80° C. to room temperature. Separation of the lower layer gave 99 grams of the desired (TFEO)$_8$ diacid chloride.

EXAMPLE XLV

Preparation of (TFEO)$_8$ Derived Bis(keto-ylid)

A three-liter, three-necked flask was equipped with a magnetic stirrer, thermowell, condenser, an addition funnel, and a gas outlet leading to a nitrogen by-pass and through a bubbler. The flask was charged with benzyl triphenylphosphonium chloride (164 grams), ethyl ether (1.5 liters) and was flushed with dry nitrogen before the butyllithium (167 grams) was added over a one-hour period. The development of a bright orange color indicated a reaction. The mixture was stirred for one hour before the (TFEO)$_8$ diacid chloride (67 grams) was added. After the addition was complete, a light tan slurry was left. The solids were removed by filtration and the solvent was evaporated to give a dark brown liquid. After treatment of this liquid with hexane a light brown powder was collected. A total of 82 grams of bis(keto-ylid) was collected for a 71% yield.

EXAMPLE XLVI

Chlorination of (TFEO)$_8$ Derived Bis(keto-ylid)

A 250-ml, three-necked flask was equipped with a Dry-Ice condenser, a thermometer, and a gas inlet. The (TFEO)$_8$ derived bis(keto-ylid), 16.2 grams, was dissolved in 100 ml of Freon 113 before being added to the dry flask. The system was swept with dry nitrogen. Chlorine was bubbled in over a 30-minute period as an exotherm to 40° was noted. The chlorine was passed through a column of molecular sieves to remove any HCl present before being bubbled into the solution. The lower layer was separated and the Freon removed to give 8.7 grams of slightly yellow oil. After adding fresh Freon 113 the material was passed through a column of silica gel and alumina to give a clear oil (8.1 grams) which represents a 68% yield.

EXAMPLE XLVIa

Chlorination of (TFEO)$_8$ Derived Bis(Keto-ylid)

The chlorination was repeated using 27.5 grams of the (TFEO)$_8$ derived bis(keto-ylid). The reaction was carried out as described in the previous chlorination, and workup gave 14.5 grams of slightly yellow oil after being passed through a silica gel column.

EXAMPLE XLVIb

Chlorination of (TFEO)$_8$ Derived Bis(keto-ylid)

The chlorination was repeated using 25 grams of the (TFEO)$_8$ derived bis(keto-ylid). Following work-up through a column of alumina and silica gel, 16 grams of the (TFEO)$_8$ desired tetrachlorodiketone was collected. This represents an 89% yield from the bis(keto-ylid).

EXAMPLE XLVII

Preparation of (TFEO)$_8$ Derived Tetraketone

Figure 8:
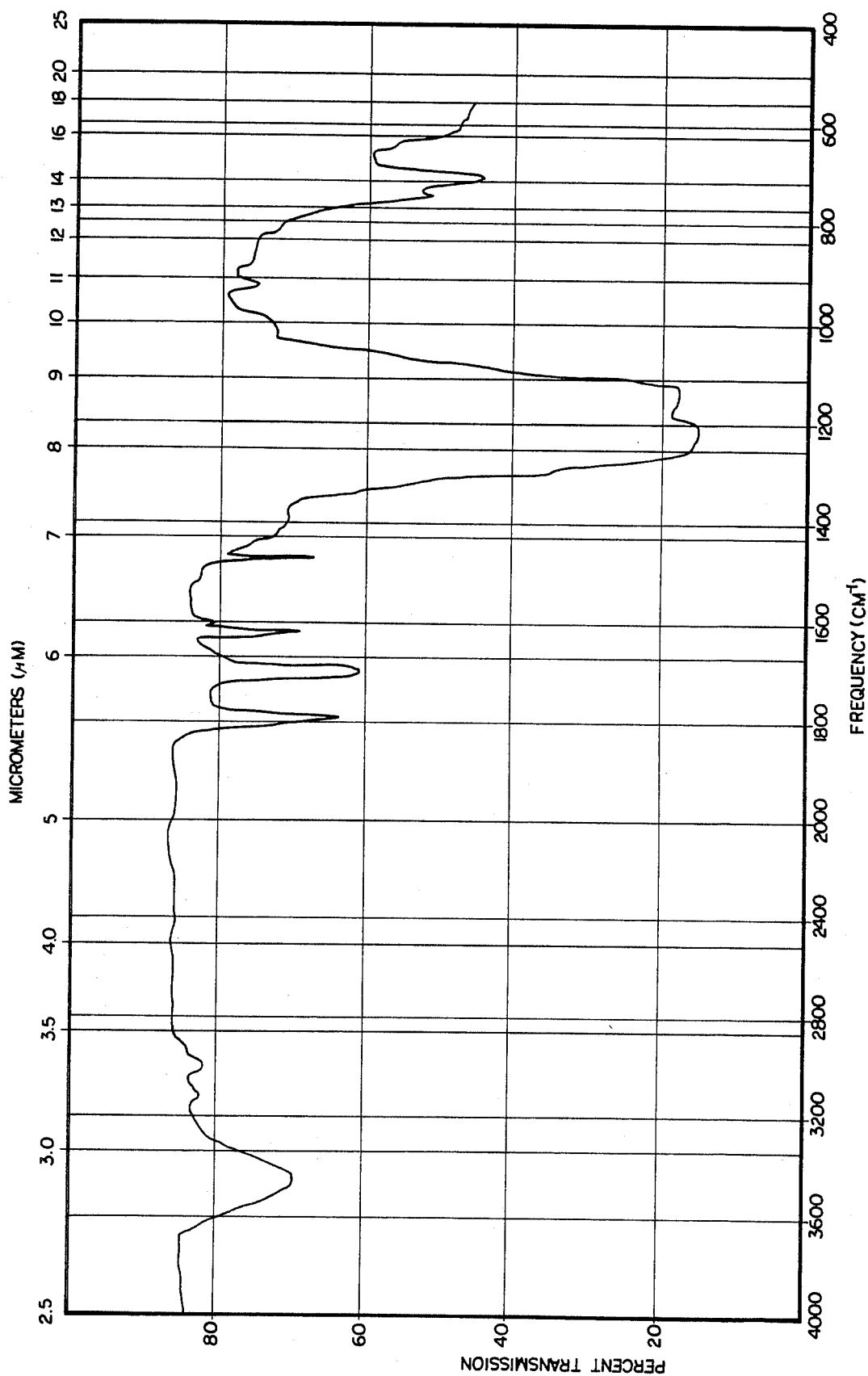
FIG. 8 is a liquid smear scan of the product of Example XLVII.

A 250-ml, three-necked flask was equipped with a magnetic stirrer, thermometer, heating mantle, and condenser backed by a liquid oxygen trap. The (TFEO)$_8$ derived tetrachlorodiketone, 11 grams, was added to the acetonitrile (100 ml) along with silver trifluoroacetate (5.3 grams) and water (0.5 ml). The mixture was stirred as the solution was heated to reflux over a 20-hour period. After cooling the mixture to ambient temperature, the silver salts were filtered out and the solvent removed under full vacuum. The remaining yellow oil was taken-up in Freon 113 and passed through a column of alumina and silica gel. Removal of the Freon 113 gave 6.7 grams of a bright yellow oil which was identified as the tetraketone, C$_6$H$_5$C(O)C(O)(CF$_2$OCF$_2$)$_7$C(O)C(O)C$_6$H$_5$, by infrared analysis and mass spectrometry. (FIG. 8).

What is claimed is:

1. A process for making a quinoxaline which comprises the steps of:
   (a) reacting a phosphorane with an acid halide of a polyoxy perfluoro-alkylene oxide wherein the perfluoro-oxyalkylene group has 2 or 3 carbon atoms and the number of perfluoro-oxyalkylene units is in the range of 2 to 20, to form a keto-ylid;
   (b) chlorinating said keto-ylid to form a polychloroketone;
   (c) hydrolyzing said polychloroketone to form the corresponding polyketone have one or two

groups therein; and
   (d) reacting said polyketone with an o-arylene diamine to form the corresponding quinoxaline.

2. A process as defined in claim 1 in which the phosphorane is benzyl triphenyl phosphorane.

3. A process as defined in claim 1 wherein the perfluoro-oxyalkylene group has two carbon atoms.

4. A process as defined in claim 1 wherein the polyoxy-perfluoroalkylene oxide is derived from tetrafluoroethylene oxide.

5. A process as defined in claim 1 wherein the keto-ylid is a bis-keto-ylid and the polychloroketone is a bis(alpha, alpha-dichloroketone).

6. A process as defined in claim 5 wherein the polyketone has two

groups therein.

7. A process as defined in claim 1 wherein the quinoxaline is a bis-quinoxaline.

8. A process as defined in claim 1 wherein the perfluoro-oxyalkylene group has three carbon atoms.

9. A process as defined in claim 1 wherein the polyoxy-perfluoro-alkylene oxide is derived from hexafluoro-propylene oxide.

10. A process as defined in claim 1 wherein the keto-ylid is a monoketo-ylid and the polychloroketone is an alpha, alpha-dichloroketone.

11. A process as defined in claim 10 wherein the polyketone has one

group therein.

12. A process as defined in claim 1 wherein the acid halide is the acid chloride.

13. A process as defined in claim 1 wherein the chlorinating agent is elemental chlorine.

14. A process as defined in claim 1 wherein the chlorinating agent is thionyl chloride.

15. A process as defined in claim 1 wherein the dechlorinating agent is silver trifluoroacetate.

16. A process as defined in claim 1 wherein the o-arylene diamine is o-phenylene diamine.

17. A process for making a polychloroketone which comprises the steps of:
    (a) reacting benzyl triphenyl phosphorane with an acid halide of a polyoxy-perfluoro-alkylene oxide wherein the perfluoro-oxyalkylene group contains 2 or 3 carbon atoms and the number of perfluoro-oxyalkylene units is in the range of from 2 to 20, to form a keto-ylid; and
    (b) and chlorinating said keto-ylid to form a polychloroketone.

18. A process as defined in claim 17 wherein the perfluoro-oxyalkylene group contains two carbon atoms.

19. A process as defined in claim 17 wherein the polyoxy-perfluoroalkylene oxide is derived from tetrafluoro-ethylene oxide.

20. A process as defined in claim 17 wherein the keto-ylid is a bis-keto-ylid and the polychloroketone is a bis(alpha, alpha-dichloroketone).

21. A process as defined in claim 20 wherein the polyketone has two

groups therein.

22. A process as defined in claim 17 wherein the perfluoro-oxyalkylene group contains three carbon atoms.

23. A process as defined in claim 17 wherein the polyoxy-perfluoroalkylene oxide is derived from hexafluoro-propylene oxide.

24. A process as defined in claim 17 wherein the keto-ylid is a mono-keto-ylid and the polychloroketone is an alpha, alpha-dichloroketone.

25. A process as defined in claim 17 wherein the acid halide is the acid chloride.

26. A process as defined in claim 17 wherein the chlorinating agent is elemental chlorine.

27. A process as defined in claim 17 wherein the chlorinating agent is thionyl chloride.

28. A process for producing a perfluoro-1,2-diketone which comprises the steps of hydrolyzing a perfluoro-poly-chloroketone, with water and silver trifluoroacetate and recovering the 1,2-diketone.

* * * * *